(12) United States Patent
Watson et al.

(10) Patent No.: US 9,254,090 B2
(45) Date of Patent: Feb. 9, 2016

(54) TISSUE CONTRAST IMAGING SYSTEMS

(75) Inventors: Jason Paul Watson, San Jose, CA (US); Vahid Saadat, Atherton, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/278,820

(22) Filed: Oct. 21, 2011

(65) Prior Publication Data

US 2012/0150046 A1    Jun. 14, 2012

Related U.S. Application Data

(60) Provisional application No. 61/406,065, filed on Oct. 22, 2010.

(51) Int. Cl.
  *A61B 6/00*    (2006.01)
  *A61B 5/00*    (2006.01)
  *A61B 1/04*    (2006.01)

(52) U.S. Cl.
  CPC .............. *A61B 5/0084* (2013.01); *A61B 1/043* (2013.01); *A61B 5/0071* (2013.01); *A61B 5/6852* (2013.01)

(58) Field of Classification Search
  CPC .. A61B 5/0084; A61B 5/0071; A61B 5/6852; A61B 1/043
  USPC .................................................. 600/473–480
  See application file for complete search history.

(56) References Cited

U.S. PATENT DOCUMENTS

| | | | | |
|---|---|---|---|---|
| 7,860,555 | B2 * | 12/2010 | Saadat | 600/476 |
| 7,918,787 | B2 * | 4/2011 | Saadat | 600/129 |
| 8,050,746 | B2 * | 11/2011 | Saadat et al. | 600/476 |
| 8,221,310 | B2 * | 7/2012 | Saadat et al. | 600/129 |
| 2006/0184048 | A1 * | 8/2006 | Saadat | 600/478 |
| 2007/0287886 | A1 * | 12/2007 | Saadat | 600/115 |
| 2007/0293724 | A1 * | 12/2007 | Saadat et al. | 600/156 |
| 2008/0009747 | A1 * | 1/2008 | Saadat et al. | 600/471 |
| 2008/0015445 | A1 * | 1/2008 | Saadat et al. | 600/470 |
| 2008/0015569 | A1 * | 1/2008 | Saadat et al. | 606/41 |
| 2008/0058591 | A1 * | 3/2008 | Saadat et al. | 600/109 |
| 2008/0058650 | A1 * | 3/2008 | Saadat et al. | 600/478 |
| 2009/0054803 | A1 * | 2/2009 | Saadat et al. | 600/546 |
| 2009/0221871 | A1 * | 9/2009 | Peh et al. | 600/118 |
| 2010/0004506 | A1 * | 1/2010 | Saadat | 600/109 |
| 2011/0060227 | A1 * | 3/2011 | Saadat | 600/476 |
| 2012/0004577 | A1 * | 1/2012 | Saadat et al. | 600/587 |

* cited by examiner

*Primary Examiner* — Sanjay Cattungal

(57) ABSTRACT

Tissue contrast imaging systems are described which detect differences in tissue contrasts to obtain images of the tissue region. The systems may be used to obtain images of the cardiac tissues particularly in a blood-filled environment.

29 Claims, 12 Drawing Sheets

TISSUE CONTRAST IMAGING SYSTEMS

CROSS-REFERENCE TO RELATED APPLICATIONS

This application claims the benefit of priority to U.S. Prov. App. 61/406,065 filed Oct. 22, 2010, which is incorporated herein by reference in its entirety.

FIELD OF THE INVENTION

The present invention relates generally to catheter imaging devices and methods of use utilizing tissue contrast under various forms of illumination to obtain images of tissue.

BACKGROUND OF THE INVENTION

Conventional devices for accessing and visualizing interior regions of a body lumen are known. For example, various catheter devices are typically advanced within a patient's body, e.g., intravascularly, and advanced into a desirable position within the body. Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, many of the conventional catheter imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895,417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. The absence of real-time visualization also poses the risk of incorrect placement and ablation of structures such as sinus node tissue which can lead to fatal consequences.

SUMMARY OF THE INVENTION

The use of fluorescence imaging is well known in medicine, e.g. Fluorescein angiography, fluorescence-guided tumor resection, etc. Fluorescence imaging has three fundamental components that can provide discrimination: (1) the excitation source, (2) the fluorophore, and (3) a filtered receiver. The excitation source can be tailored to preferentially excite one type of fluorophore over another. Various fluorophores can be introduced that preferentially occur or accumulate in one type of tissue over another. Different filters may be used to better discriminate between one fluorophore over another.

In the particular example of cardiac tissue, portions of the endocardium are covered with a thin layer of very pale tissue, and this pale tissue may mask the changes in the appearance of the endocardium that occur when the tissue has been exposed to high power RF energy (as is typically done for RF ablation therapy for cardiac arrhythmias and as described above). Potential uses of fluorescence imaging in this case include autofluorescence, where the naturally occurring fluorescence of the cardiac tissues is altered by the ablation process. Different tissues have different amounts of fluorescent species, and these differences can be exploited to improve the contrast between tissues. Another use of fluorescence imaging involves the use of injected fluorophores. For instance, examples include the use of fluoresein injections which perfuse the vasculature. Ablated tissue has coagulated and necrotic vasculature which will result in lower accumulation of fluoresein, and lower emitted signals once fluorescin is excited signals.

Another example involves the use of aminolevulinic acid injections. Aminolevulinic acid is a precursor to a family of fluorophores that are naturally produced in cells. Once injected, the aminolevulinic acid travels throughout the body and is taken up by cells, and converted into fluorescent porphyrins. The rate of this process is related to the metabolism of the cell, so that healthy cells will have a stronger fluorescence signal than ablated cells. Additionally, degradation of the fluorophores during the ablation process is also possible.

Thus, an imaging catheter may be used intravascularly not only for imaging the tissue region in vivo with direct imaging but also for irradiating the tissue with an excitation light source as well as detecting any resulting fluorescence. Generally, the imaging catheter may comprise a flexible catheter suitable for intravascular advancement, a hood attached to a distal end of the catheter and also defining an open area when the hood is in an expanded configuration, wherein the open area is in fluid communication with a fluid lumen defined through the catheter and with a blood-filled environment through an opening defined by the hood, an imager in proximity to the open area wherein the imager is positioned to visualize a tissue region adjacent to the open area, and, a sensor in proximity to the open area wherein the sensor is configured to detect fluorescence from the tissue region.

In use, the catheter may be utilized to identify the presence of perfusion in the imaged tissue region (and thus tissue regions with complete or partial ablation). An example of identifying perfusion in a tissue region of interest may generally comprise positioning a hood attached to a flexible catheter in proximity to a tissue region of interest, the hood having an expanded configuration which defines an open area which is in fluid communication with a fluid lumen through the catheter and with an environment external to the hood through an opening defined by the hood, introducing a transparent fluid into the open area via the fluid lumen such that an opaque fluid within the open area is displaced through the opening of the hood and into the environment, and illuminating the tissue region of interest adjacent to the opening of the hood via an excitation source such that any fluorophores in the tissue region fluoresce.

In other variations, rather than utilizing the hood attached to the distal end of the catheter and visualizing through the open area of the hood, the hood may be omitted from the catheter and the sensor may be positioned in proximity to the distal end such that the sensor is configured to detect fluorescence from the tissue region directly through the blood. Thus in use, perfusion in the tissue region may be accomplished by positioning the distal end of a flexible catheter in proximity to the tissue region of interest, illuminating the tissue region of interest adjacent to the distal end of the catheter via an excitation source such that any fluorophores in the tissue region fluoresce, and detecting a presence of perfusion in the tissue region upon an indication of fluorescence emitted from the tissue region.

In yet another variation, the distal end of the sensor can directly touch the tissue and acquire the signal through this close coupling.

BRIEF DESCRIPTION OF THE DRAWINGS

FIGS. 12A to 12C show partial cross-sectional side views of a region of tissue which is only partially ablated through.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
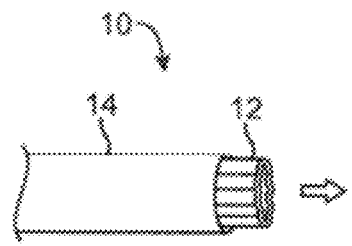
FIG. 1A shows a side view of one variation of a tissue imaging apparatus during deployment from a sheath or delivery catheter.
Figure 1B:
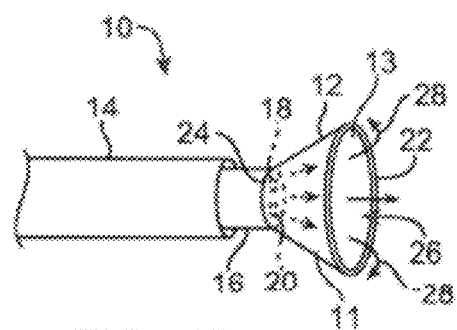
FIG. 1B shows the deployed tissue imaging apparatus of FIG. 1A having an optionally expandable hood or sheath attached to an imaging and/or diagnostic catheter.
Figure 1C:
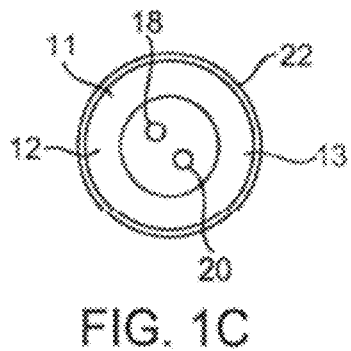
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intraatrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, DE), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
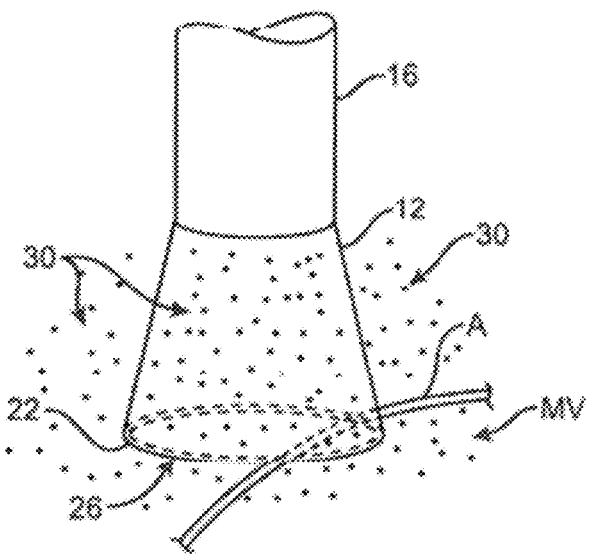
FIGS. 2A and 2B show one example of a deployed tissue imager positioned against or adjacent to the tissue to be imaged and a flow of fluid, such as saline, displacing blood from within the expandable hood.
Figure 2B:
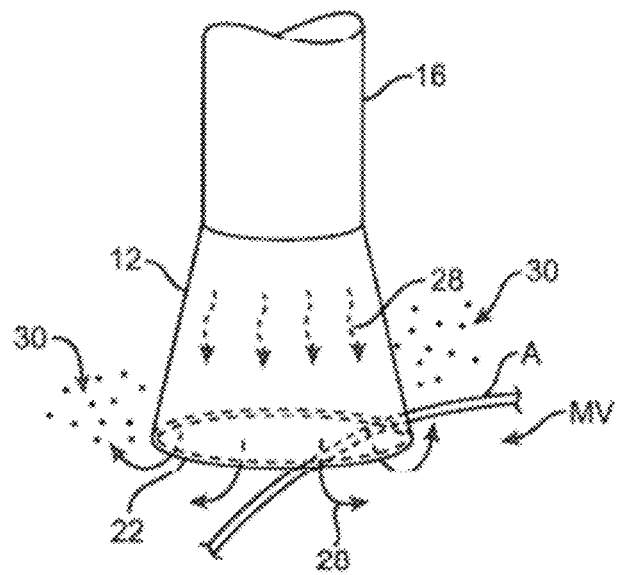

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant back-flow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure.

The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
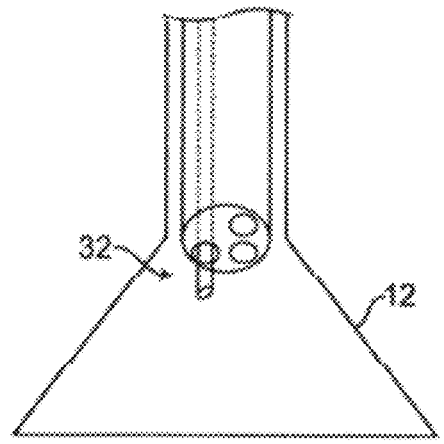
FIGS. 3A and 3B show examples of various visualization imagers which may be utilized within or along the imaging hood.
Figure 3B:
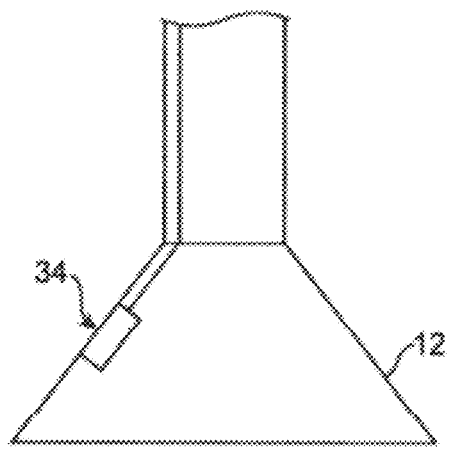

FIG. 3A shows a partial cross-sectional view of an example where one or more optical fiber bundles serve as an imager 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
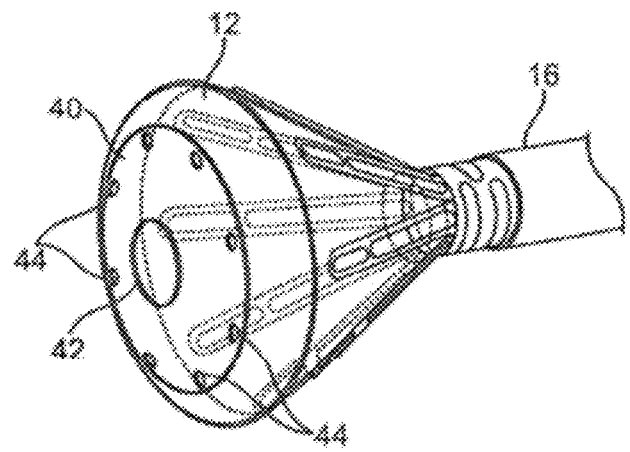
FIGS. 5A and 5B show perspective and end views, respectively, of an imaging hood which includes a membrane with an aperture defined therethrough and a plurality of additional openings defined over the membrane surrounding the aperture.
Figure 5B:
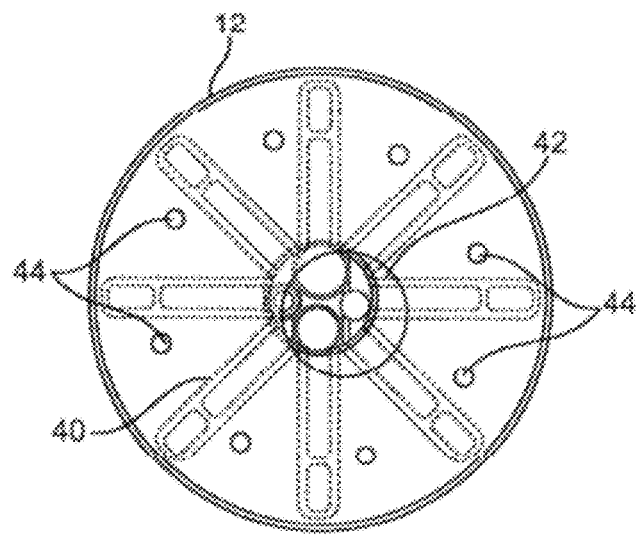

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. 2006/0184048 A1), which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety. Further details of tissue ablation utilizing the transfer of energy through the transparent fluid while under direct visualization through the hood open area which may be used with the tissue imaging described herein is shown in U.S. patent application Se. No. 12/118,439 filed May 9, 2008 (U.S. Pat. Pub. US 2009/0030412 A1), which is also incorporated herein by reference in its entirety.

In developing a vision-catheter as described above that allows for visualization of various tissues, particularly those tissues (such as cardiac tissue) that are normally surrounded in opaque media, e.g. blood, it is commonly desired to discriminate between different types of tissue states, such as healthy, necrotic, scarred, and cancerous. In one example where visual tissue state differentiation is useful is during tissue ablation such as treatment for atrial fibrillation. During and/or after ablation treatment, a visual distinction between regions of tissue which have been sufficiently ablated and regions of tissue which may still need ablation treatment or require further ablation treatment may be useful. Under typical conditions with white light illumination and standard color cameras, visual discrimination may be difficult. In these cases, a number of alternate illumination and recording schemes may be employed to improve the contrast between the tissue types of interest. Two categories of these schemes, fluorescence imaging and tailored spectrum imaging, as described in further detail below, may be utilized.

Generally, as described above, the catheter hood may be purged with saline or other fluid in order to displace an opaque fluid such as blood and allow for optical imaging through the transparent saline. Light is provided to the distal end of the catheter in order to illuminate the adjacent tissue structures of interest. The tissue structures may be observed via a system of lenses attached to an image capturing system, e.g. CMOS or CCD camera or imaging fiber bundle, that is also located at the distal end of the catheter.

The use of fluorescence imaging is well known in medicine, e.g. Fluorescein angiography, fluorescence-guided tumor resection, etc. Fluorescence imaging has three fundamental components that can provide discrimination: (1) the excitation source, (2) the fluorophore, and (3) a filtered receiver. The excitation source can be tailored to preferentially excite one type of fluorophore over another. Various fluorophores can be introduced that preferentially occur or accumulate in one type of tissue over another. Different filters may be used to better discriminate between one fluorophore over another. In the particular example of cardiac tissue, portions of the endocardium are covered with a thin layer of very pale tissue, and this pale tissue may mask the changes in the appearance of the endocardium that occur when the tissue has been exposed to high power RF energy (as is typically done for RF ablation therapy for cardiac arrhythmias and as described above). Potential uses of fluorescence imaging in this case include autofluorescence, where the naturally occurring fluorescence of the cardiac tissues is altered by the ablation process. Different tissues have different amounts of fluorescent species, and these differences can be exploited to improve the contrast between tissues. Another use of fluorescence imaging involves the use of injected fluorophores. For instance, examples include the use of fluoresein injections which perfuse the vasculature. Ablated tissue has compromised or necrotic vasculature which will result in lower accumulation of fluoresein, and lower signals. Another example involves the use of aminolevulinic acid injections. Aminolevulinic acid is a precursor to a family of fluorophores that are naturally produced in cells. Once injected, the aminolevulinic acid travels throughout the body and is taken up by cells, and converted into fluorescent porphyrins. The rate of this process is related to the metabolism of the cell, so that healthy cells will have a stronger fluorescence signal than ablated cells. Additionally, degradation of the fluorophores during the ablation process is also possible.

Figure 4A:
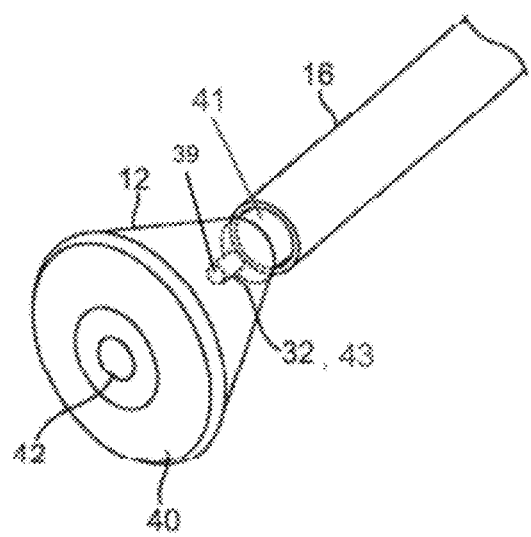
FIGS. 4A and 4B show perspective and end views, respectively, of an imaging hood having at least one layer of a transparent elastomeric membrane over the distal opening of the hood.
Figure 4B:
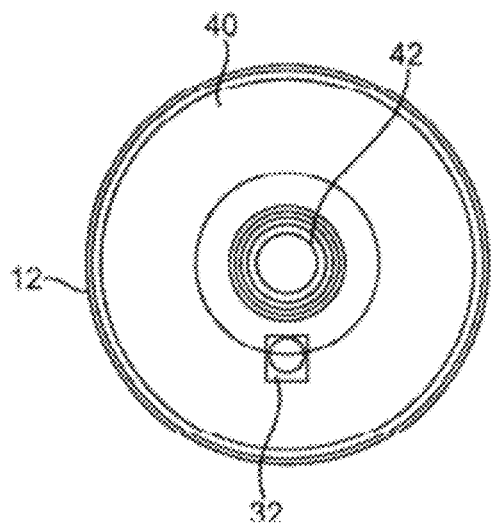

Either the excitation wavelengths or the filter wavelengths may be altered to improve discrimination. Thus, multiple cameras with different filters may be employed in the catheter 16 or imaging element, as described above, simultaneously in order to build up images that can be mathematically manipulated by the processor in communication with the catheter 16 and/or imaging element to improve discrimination. For example, three different images taken simultaneously could be mapped to the red, green, and blue channels of a standard video. The different images could be taken with a single camera sensor, such as sensor 43 positioned in catheter 16 (as shown in FIG. 4A) that has a specific mosaic of filters 39 applied to its various pixels, much like the Bayer patterns used in standard CMOS imagers. Alternatively, fluorescence images could be interleaved with standard visible imaging in order to highlight specific types of tissue, or multiple fluorescence images with different excitation sources and/or imaging filters could be interleaved to build up a composite video signal with improved discrimination.

Another method related to fluorescence imaging involves replacing the fluorescent species with radioactive species. The methods of discrimination are the same as with fluorescent species, however the detection techniques are different. In this case, a scintillation layer or other radiation sensor layer could be applied to or incorporated into the distal-most portion of the hood or other body. The image sensor 43 could then see the activity from the scintillation layer superimposed on the underlying tissue when visualized through the saline fluid. Alternatively, the radio-sensitive layer could be applied in close proximity to the distal image plane, and the distal portion of the catheter 16 and/or the image sensor housing could be made radio-opaque except for a distal opening facing the tissue, e.g. the aperture of the imaging system. In this case, the radio-sensitive layer will get signals from the area of the tissue that is being imaged.

Figure 6:
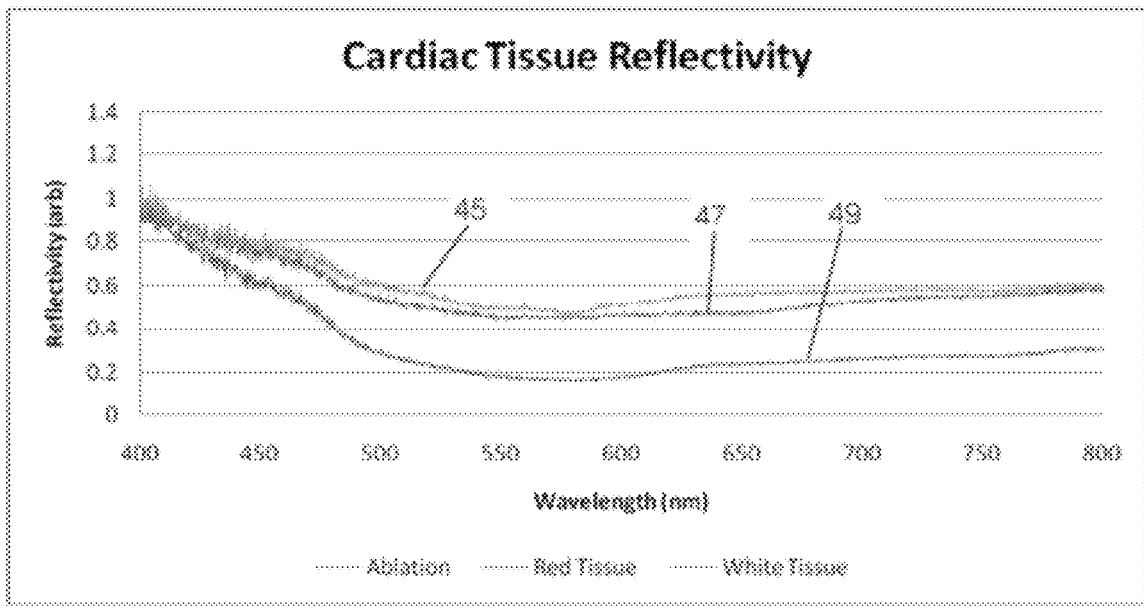
FIG. 6 shows an example of the relative reflectivity of different tissue types in distinguishing between the different states of tissue.

In contrast to fluorescence imaging, which achieves contrast by different types of light emission, tailored spectrum imaging relies on differences in reflection, absorption, and transmission between tissue types in order to maximize perceived differences in an image of the tissues. Due to differences in their chemical makeup, different tissues have differences in their reflection, transmission, and absorption (RTA) spectra. However, these differences are often very slight, and so when the tissue types are illuminated by broad-spectrum light and the image is captured by standard, RGB cameras, these slight differences are easily washed out. However, by tailoring the illumination and/or the camera responsivity to better match the spectral regions where the differences lie, the contrast between different tissue types can be improved. Taking for example the previous case of cardiac tissue with a thin layer of white tissue that reduces the contrast between healthy tissue and ablated tissue, the reflectivity of the different tissue types is represented in FIG. 6, which illustrates the relative reflectivity of the different tissue types and states over the range of visible light, e.g., 400 nm to 800 nm. For instance, although the reflectively 45 of the ablated tissue is sufficiently different from the reflectivity 49 of healthy red tissue to provide for visual discrimination over the range of visible light, the reflectivity 45 of ablated tissue is relatively close to the reflectivity 47 of the thin layer of healthy white tissue which makes for visual discrimination relatively more difficult between these two tissues.

Figure 7:
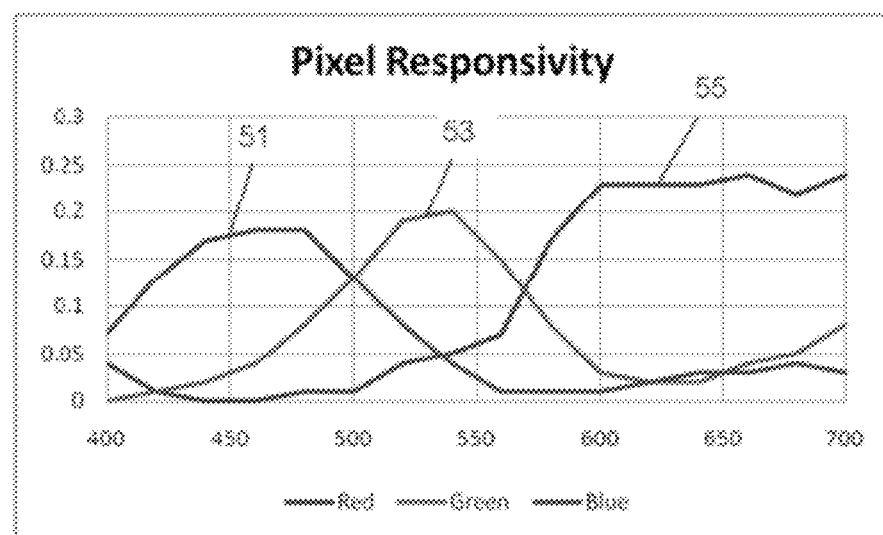
FIG. 7 shows an example of the pixel responsivity of RGB pixels in a CMOS camera.

Additionally, the responsivity of a typical set of RGB pixels in a CMOS camera is shown in FIG. 7 where the pixel responsivity of blue light is shown by curve 51, green light is shown by curve 53, and red light is shown by curve 55. In this case, the difference between the two tissues is minimized in the green-yellow region, which is precisely the peak of the visual response, and of typical, daylight-mimicking light sources. Enhancing the illumination in the deep blue area (~450 nm) and deep red area (~650 nm) would result in a greater difference in the image of the two tissue types. The level of green light (~525 nm) could then be adjusted to preserve the overall white balance of the illumination. Alternatively, standard images could be interleaved (where the interleaving method can include both temporal and spatial methods) with images taken at a specific wavelength, e.g. deep red. The images taken at a specific wavelength could be used to enhance or highlight the standard color images. As a further alternative, multiple images at specific wavelengths could be taken in an interleaved fashion and recombined in a variety of methods in order to improve contrast.

The visualization catheter described herein could implement these techniques, such as to deliver specific illumination profiles, and how to interleave/multiplex different images. Illumination may be delivered in two general categories: distal generation and proximal injection. In the former case, light is generated at the distal end of the catheter device 16, most commonly by one or more LEDs, such as excitation source 41 shown in FIG. 4A. LEDs have generally discrete wavelengths, which make them well suited to the applications described previously. They can also be modulated electrically at rates of speed that are well above the frame rates of standard video cameras, which also makes them suitable for illuminating temporally multiplexed video frames. In the case where more discrete wavelengths are required or when higher spatial brightness is required, LEDs could be replaced with diode lasers or super-luminescent diodes (SLEDs). In the other illumination case, light is injected at the proximal end of the catheter and delivered to the distal end by some light guide, such as fiber optic bundles. In this case the size constraints are relaxed, and so in addition to the light sources mentioned for use in the distal end, other sources such as filtered broad-band emitters (xenon lamps) are possible. These filtered sources can be reconfigured readily, potentially allowing them to be used in multiplexing situations.

Imaging can be implemented in the catheter in two broad categories, based on the location of the image capture sensor. In the case where the sensor is positioned distally, size constraints generally require that the sensor be a single array of pixels. Multiplexing in this case can be achieved in two distinct ways (which can also be combined): spatial and temporal. In the spatial case, a pattern of one or more filters 39 with transmission peaks corresponding to one or more of the wavelengths is applied over the one or more pixels of the camera 32 such that a difference in the image of the tissue region may be further increased. Typically these filters broadly correspond to red, green, and blue, but for the purposes of tissue contrast, some or all of these filters can be narrow. Additionally, some pixels may be left unfiltered, in order to provide a general illumination level for later reconstruction of a video signal. In the case of temporal multiplexing, the frame rate of the camera is increased to a higher multiple of the standard video frame rate (typically ~30 Hz). When combined with a temporally multiplexed illumination source, images taken under different illumination conditions are integrated into a single video stream with improved contrast.

In the case where the sensor is positioned proximally, the image is first formed via distal optics, and then relayed to the proximal end via optical means, e.g. imaging fiber bundles, and then projected on the image sensor. As with the illumination category, when the sensor is positioned proximally, size constraints are relaxed. Multiplexing can be accomplished in all the aforementioned ways, as well as by splitting the light between multiple cameras.

Figure 8A:
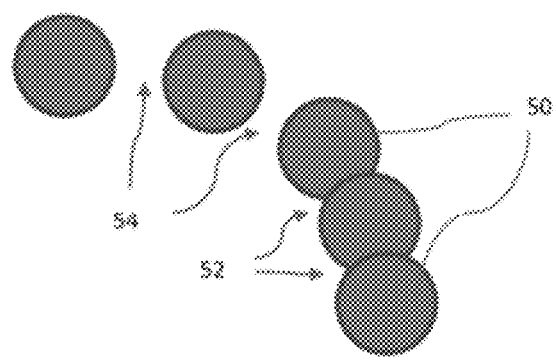
FIG. 8A illustrates an example of a region of tissue which has undergone tissue ablation to form a segment with a contiguous conduction block and a segment with a segments of non-ablated tissue.

In one example for utilizing either of the imaging techniques described above, FIG. 8A illustrates a region of tissue which has undergone tissue ablation. The discrete lesions 50 formed by ablation treatment through the catheter hood is shown in one region as a contiguous line of ablation where each discrete lesion 50 is overlapped 52 with an adjacent lesion 50 to form a conduction block. Regions where the discrete lesions 50 have gaps 54 between form a non-overlapping insufficient conduction block with missing segments which may allow for errant electrical signals to pass through the tissue. Further details of forming the regions of ablated tissue with the hood are described in U.S. patent application Ser. No. 12/118,439, which has been incorporated by reference in its entirety hereinabove.

Figure 9:
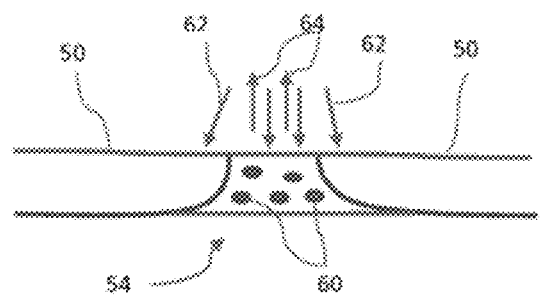
FIG. 9 illustrates a cross-sectional side view of a non-ablated tissue segment fluorescing between adjacent segments of ablated tissue.

To visually distinguish and identify the spaces between the ablated tissue 50 and the non-ablated tissue gaps 54, imaging with, e.g., fluorescence, may be employed. The illustration shown in FIG. 9 shows a cross-sectional side view of a gap 54 of non-ablated tissue positioned between two adjacent discrete lesions 50. Any of the fluorophores 60 described above may be introduced into the tissue (such as via dyes injected intravenously into the patient, direct injection of a dye into the tissue of interest through a needle advanced from the catheter, through the hood, and into the underlying tissue, or by infusion of a dye containing the fluorophores from the hood and into the underlying tissue, etc.) through the imaging hood 12 such that fluorophores 60 preferentially form within the non-ablated tissue within the gap 54. When the excitation source (such as source 41 shown in FIG. 4A) emits an illumination 62 at one or more discrete wavelengths from the catheter 16, the light may be absorbed by the fluorophores 60 present in the non-ablated tissue 54 such that the fluorophores 60 begin to fluoresce and emit fluorescent light energy 64 visibly distinguishable by the viewer from the non-fluorescing tissue of the ablated regions 50. Various fluorophores may be utilized such as endoscein, fluorescein, fluorescein derivatives, Methylene blue, indocyanine green, etc.

Figure 8B:
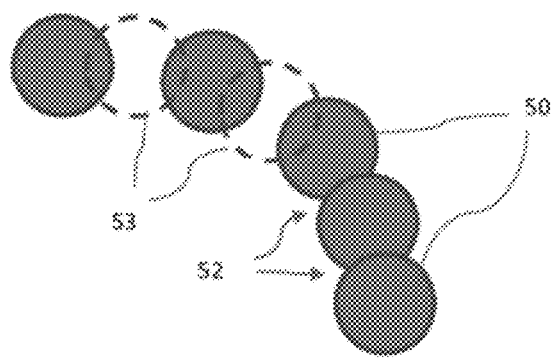
FIG. 8B illustrates another example where the gaps of non-ablated tissue may be identified via fluorescence and then ablated to form a contiguous lesion.

Once the non-ablated tissue has been distinguished or characterized relative to the ablated tissue via the fluorescence or radiation difference, the hood (and/or other ablation instrument positioned within the hood) may be moved to the regions of non-ablated tissue. The non-ablated tissue forming the gaps 54 may then be ablated with additional lesions 53 to form the overlapping 52 ablated regions such that the lesions 50 are contiguous to form a sufficient conduction block, as shown in FIG. 8B.

Figure 10:
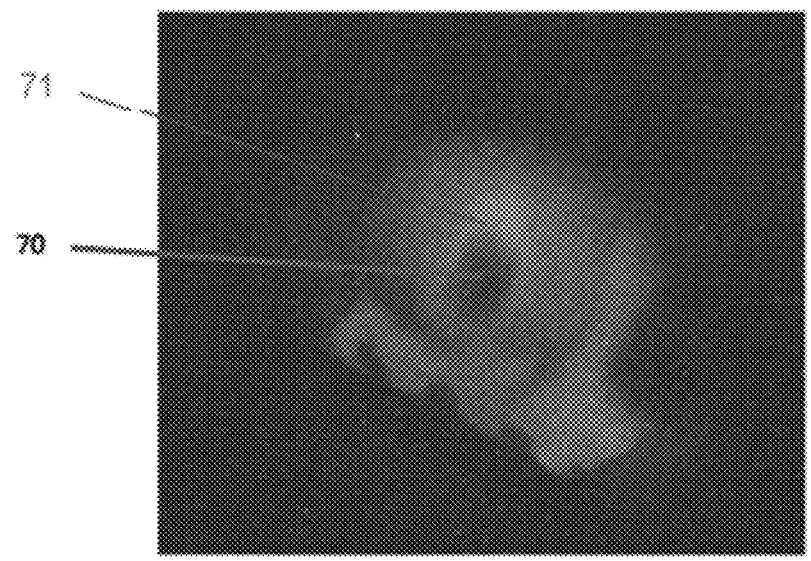
FIG. 10 shows an example of a formed lesion under fluorescence having a relatively bright border and a darkened center indicative of a central ablated region with comprised vasculature and a border region with blood/fluid accumulation.
Figure 11:
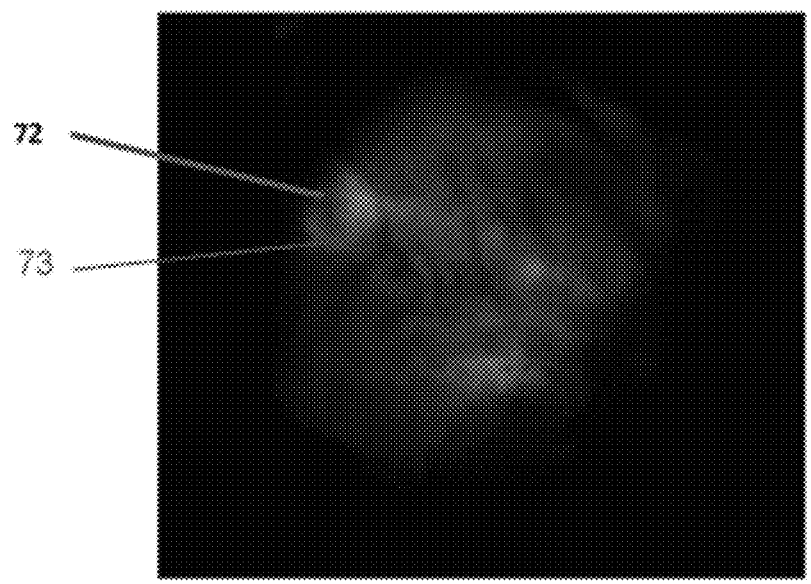
FIG. 11 shows another example of a formed lesion under fluorescence having little or no relative darkened areas indicative of an overabundance of edema and little or no necrosis.

The lesions in tissue formed by RF ablations commonly have borders that are characterized by edema and hemorrhage (hemorrhagic border) where blood and blood products typically accumulate. When the blood is perfused with fluorescent dyes, these regions can accumulate more dye molecules, and consequently emit relatively more fluorescent light than the adjacent tissue. During experiments, lesions were observed to have relatively bright borders and dark centers, e.g., as shown in FIG. 10, indicating a central ablated region 70 with compromised vasculature and a border region 71 with blood/fluid accumulation. Additionally, some lesions were observed to have little or no dark area 72, being almost entirely composed of bright areas 73, as shown in FIG. 11. This may indicate an overabundance of edema and little or no necrosis. Such lesions are considered to have relatively poorer efficacy when compared to fully ablated lesions, and so fluorescence imaging may also be used as a gauge of lesion quality.

While lesion area can be readily derived from the extent of the relatively darker area, the lesion depth can be correlated with the amount of fluorescence. This may be particularly useful in distinguishing between ablated regions of tissue which have full transmural ablations where the entire tissue thickness is ablated through and regions of tissue which do not have full transmural ablations where the tissue thickness is only partially ablated. Regions of tissue which are only partially ablated may still allow for errant electrical signals to pass through.

In utilizing visual fluorescence intensity as a gauge for determining ablation transmurality, the relatively lower amounts of fluorescence may correspond to relatively deeper ablated regions and the relatively higher amounts of fluorescence may correspond to relatively healthy or edemous tissue. The use of dyes with longer wavelengths (which penetrate farther into tissue) may be particularly useful in this calculation. Temporally resolved fluorescence can also be used to obtain information on lesion depth. By exciting the dyes with a pulsed excitation light source (e.g., ultra fast mode-locked Ti-sapphire lasers) where the pulses have a spatial extent (e.g., 100 µm spatial extent) in the propagation direction that is small relative to the tissue thickness, then the fluorescence emission may also be pulsed with different depths turning on at different times due to the differing propagation times through the tissue. Using gated detection techniques, information from different depths can be isolated.

Fluorescence imaging can also be used to more readily identify various aspects of cardiac anatomy. The amount of fluorescence from a particular structure or tissue type can be made different from neighboring tissue through several methods. Different tissue types may take up dyes at different rates due to metabolic, chemical, or structural differences. For example, fibrous regions have lower metabolic rates than muscular regions, so uptake of certain dyes will be higher in muscular regions. Alternatively, fluorescent dyes may be combined, or functionalized, with other molecules that bind preferentially or exclusively to specific types of cells in order to highlight concentrations of those cells, e.g., discern fatty tissues from muscular tissues or nerves from muscular tissue. For example, Methylene Blue is a common stain for microscopy and it has a strong fluorescence.

Alternatively, specific locations in the body may be targeted with dyes in order to glean information about those specific locations. For example, the esophagus could be coated with a fluorescent dye so that a fluorescence signal seen by a catheter that is capable of exciting the dye could correspond to the location of the esophagus relative to the chambers of the heart, allowing the esophagus to be avoided during ablation. If the dye is thermally sensitive, then ablation may proceed, even in areas with an esophageal signal, up until the point at which the signal starts to change, indicating a rise in the esophageal temperature. Other examples of uses for fluorescent tagging of specific tissue types include, e.g., tagging fat tissue to indicate areas of the cardiac wall that are backed by epicardial fat and therefore require more ablation to achieve transmurality; tagging the fatty covers of nerve bundles so that they can be avoided (such as the phrenic nerve) or targeted (such as renal nerve for relieving hypertension); tagging vulnerable arterial plaques; highlighting the aortic root for avoidance during ablation; and highlighting the septum to identify its position and thickness.

The emission and absorption spectra of fluorescent dyes are also commonly sensitive to external influences such as pH and electric fields. These sensitivities could be used to improve visualization through a number of methods by removing or filtering out the signals from any surface effects which may lead to errant visual images. For example, various obstructions or features on the surface of the tissue may provide a false image. Additionally, regions of tissue which are only partially ablated through may also provide an image which would otherwise indicate a full transmural ablation.

Figure 12A:
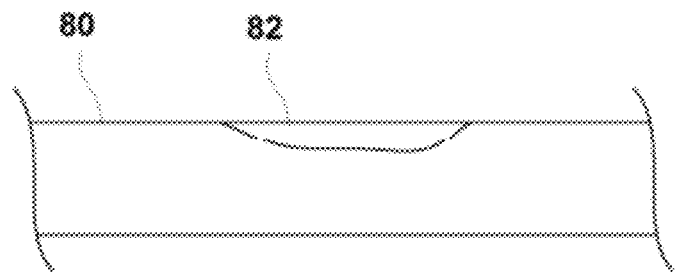
Figure 12B:
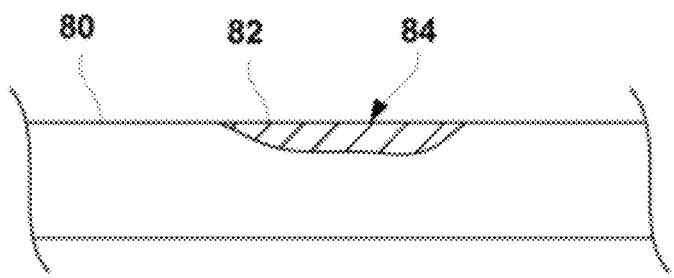
Figure 12C:
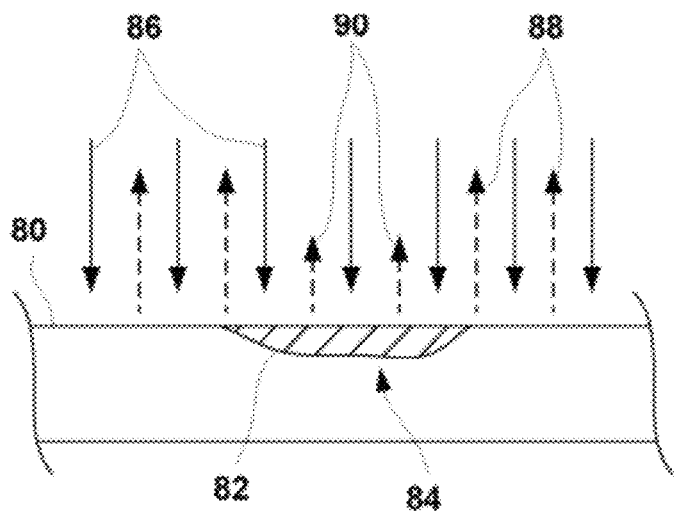

An example is illustrated in the partial cross-sectional side views of FIGS. 12A to 12C which show a region of tissue 80 which is only partially ablated 82 through. A visual image with or without fluorescence may otherwise indicate that the partially ablated tissue 82 is a full transmural ablation. To remove or mitigate the effects of partial transmural ablations and other surface effects, the tissue surface may be treated to alter its physiological characteristic, e.g., tissue pH (as described in further detail below), to artificially increase the peak response of the tissue, as illustrated by the altered lesion 84 in FIG. 12B. When the tissue 80 and partial lesion 82 are irradiated by the excitation source 86, as shown in FIG. 12C, the increased peak response may be filtered out to remove any signals from the surface tissue and thus allow the reflected signals 88 from the tissue 80 and signals 90 from the tissue underlying the partial lesion 82 to be detected indicating that the lesion 82 is only a partial transmural lesion.

As mentioned above, the sensitivity of tissue to changes in pH can be exploited by irrigating the surface of the tissue with a solution with a pH level different than blood or tissue. When combined with an fluorescence imaging system with a filter that discriminates between the different spectral properties of the dye in different pH, then surface tissue (exposed to the irrigant) can be differentiated from sub-surface tissue (exposed to blood/tissue). Additionally, since cellular metabolic by-products can alter the local pH (e.g. lactic acid production), levels of cellular activity in the heart could be quantified by a catheter-based fluorescence imaging system. Dyes may also be influenced by ultrasonic energy, so that a fluorescence image may indicate the presence and/or strength of ultrasound waves.

The use of fluorescence-based tissue categorization in the heart by a catheter can be further used to provide a general picture of the state of disease or injury to the heart. Imaging methods such as MRI or CT are used to create indices of disease state in atrial fibrillation. In addition, electrocardiogram signals are typically combined with cardiac mapping systems, such as NAVX® or Carto®, to create maps of electrical activity in order to discern disease state (as in atrial fibrillation) or injury (as in myocardial infarction induced ventricular tachycardia). Similar applications are possible with a fluorescence-based imaging catheter. When combined with cardiac mapping systems, a suite of diagnostic maps are possible, ranging from stitching multiple fluorescence images onto the volume created by the mapping system, to displaying a fluorescence-derived tissue health metric on the volume created by the mapping system. Such diagnostic tools could be used in conjunction with or in place of existing maps, either electrocardiogram based or tomography based. Furthermore, once the fluorescence map has been created, it can be used to guide planning of ablation therapy during the procedure.

Figure 13A:
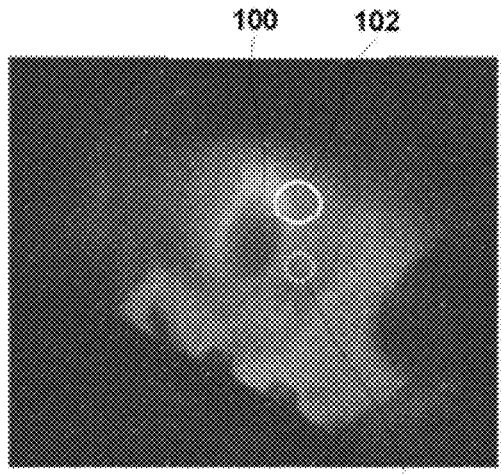
FIGS. 13A to 13F show an example of tracking lesion formation through the changes in the fluorescence intensity of the tissue.
Figure 13B:
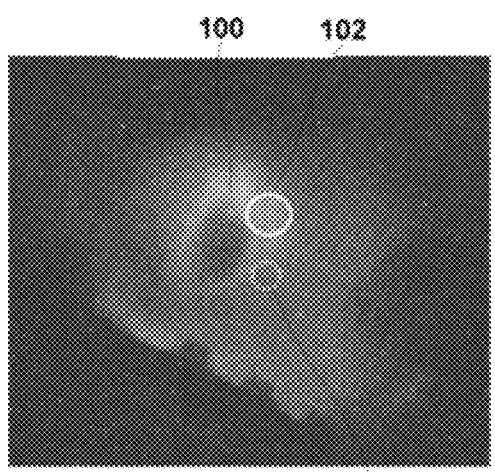
Figure 13C:
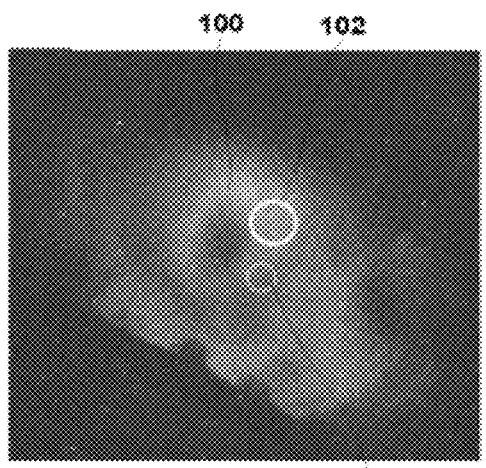
Figure 13D:
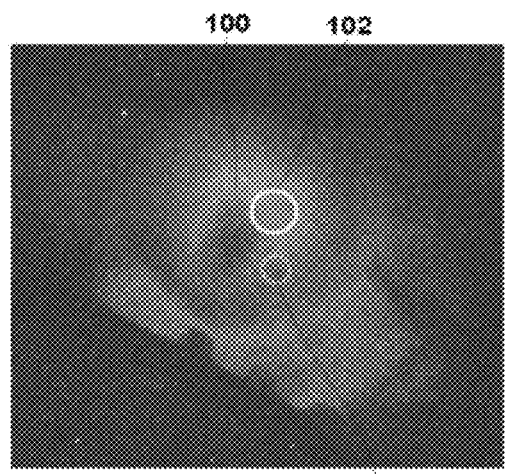
Figure 13E:
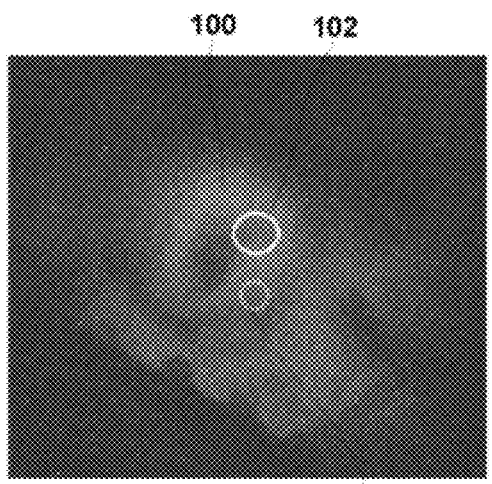
Figure 13F:
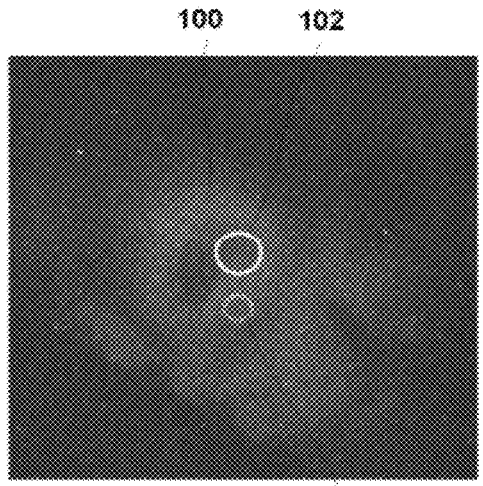

An example of tracking lesion formation through the changes in the fluorescence of the tissue is illustrated in FIGS. 13A-13F which illustrate the changes in fluorescence intensity of a region of tissue 100. For instance, FIG. 13A illustrates a first portion of tissue 102 to be ablated and a second portion of tissue 104 for comparison. As the first portion of tissue 102 is ablated, an initial increase in its fluorescence signal may be seen in FIG. 13B. The fluorescence signal of ablated tissue portion 102 may show a gradual decline in intensity over a period of time, as illustrated in FIGS. 13C to 13F, which is comparable to an adjacent lesion. In contrast, the fluorescence signal from the unablated second portion of tissue 104 may show a comparatively slower decline in signal intensity due to the excretion of the dye from the blood.

Figure 14:
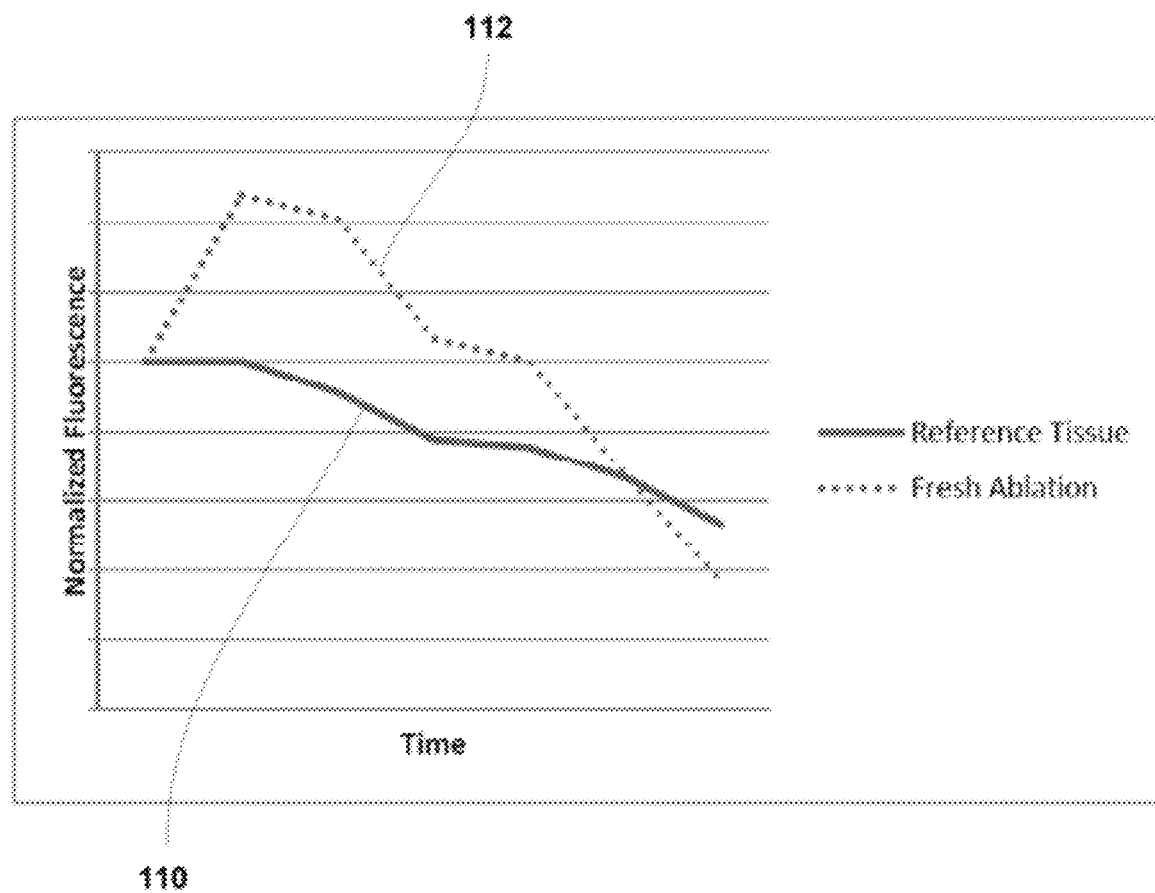
FIG. 14 shows a chart of the normalized fluorescence signal from the tissue over a period of time.

FIG. 14 illustrates a chart of the normalized fluorescence signal from the tissue over a period of time. As shown, as the fluorescence intensity 110 of the unablated second portion of tissue 104 (reference tissue) declines over time, the newly ablated first portion of tissue 102 (fresh ablation) may show an initial relative increase in fluorescence intensity 112 with a gradual decline in intensity over the same period of time. Accordingly, by comparing the relative fluorescence intensity of ablated tissue and non-ablated tissue, a determination may be made as to the ablative state of the tissue of interest.

In addition to lesion characterization, anatomical identification, and disease assessment, fluorescence-based catheter imaging can assist directly during treatments. For example, the fluorescence signal during ablation can be used to guide dosimetry. If the dye degrades or is expelled (due to tissue desiccation) during an ablation, then the reduction in fluorescence signal can be used as a therapeutic endpoint.

Figure 15:
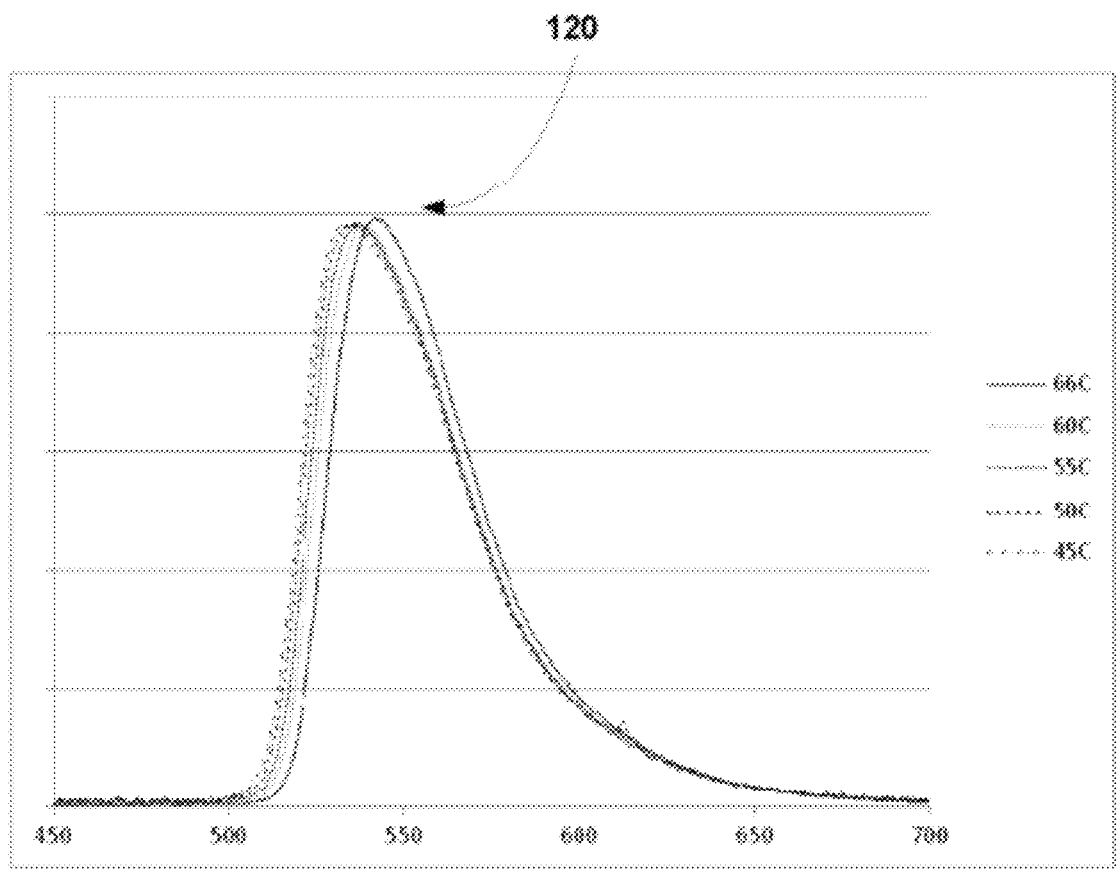
FIG. 15 shows a chart which illustrates normalized changes in fluorescence intensity over a range of temperatures during RF ablation.

If the dye has temperature dependent fluorescence, then the change in fluorescence can be used as thermometry as well. For example, the relative fluorescence intensity may be monitored during an ablation procedure as an indication of tissue temperature. FIG. 15 illustrates a chart which shows normalized changes in fluorescence intensity over a range of temperatures during RF ablation. As shown, fluorescence intensity 120 may shift on the chart as tissue temperature increases (e.g., 45° C., 50° C., 55° C., 60° C., and 66° C.). Thus, depending on the resulting intensity 120, the temperature of the tissue may be determined accordingly.

Any of these types of signals (or their derivatives in time) described above could be used as an input to an automatic power control loop in an RF generator.

Alternatively, instead of assessing the progress of an ablation, a fluorescent dye that is strongly bound to blood plasma could be used to highlight the presence of blood in the visual field (something which is more challenging under visual guidance due to the similar color of blood and muscle). Rapid and definitive identification of blood could be used to indicate good contact between the catheter and the heart wall, as well as providing a signal on which to halt the delivery of RF energy in order to prevent coagulation.

In addition, the dyes themselves may be part of the therapy. For example, the compounds used in photodynamic therapy have fluorescence properties in addition to their therapeutic properties. In this case, a fluorescence imaging catheter could be used to confirm uptake of the PDT agent, e.g. aminolevulinic acid, at the site required, and then the catheter could illuminate the tissue with the therapeutic wavelength. Dosimetry could also be confirmed via fluorescence in this case. A specific example of this case would be the homogenization of a myocardial infarction scar for the purposes of curing ventricular tachycardia (VT). In this case, isolated pockets of healthy tissue inside and at the border of an infarction scar are a source of tachycardia. The healthy tissue takes up the PDT agent more rapidly than the infracted tissue. The fluorescence image highlights the non-uniformities in the infracted region and these non-uniformities are targeted with the therapeutic light. The therapeutic light alters the properties of the PDT agent so that targeted areas no longer appear in the fluorescence image, thereby confirming the delivery of therapy. This example also has direct application in identifying and closing gaps in a pre-existing lesion set in the left or right atrium. Such a case would be commonly encountered in a second procedure to correct an atrial arrhythmia. In another example, the therapeutic agent is fluorescent, and the catheter is used to assess uptake and confirm dosage. In a further example, the therapeutic agent is fluorescent and can be denatured or otherwise rendered non-therapeutic via a catheter-delivered signal, e.g. light, and the catheter is used to assess dosimitry and control the excess dosimetry by deactivating the excess therapeutic agent. Lastly, the tissue characterization and anatomical identification abilities of a fluorescent imaging catheter system may be used to guide placement of implantable elements, such as lead placement for pacemakers (where nervous tissue identification would be useful) or anchor point for aneurysm closure devices (where assessing tissue thickness and viability would be useful).

In addition to using fluorescence imaging for tissue characterization, fluorescent dyes could be used to tag specific points in the anatomy. In this case, rather than injecting the dye into the entire body or bloodstream, the dye would be injected in small doses in localized areas, potentially through the use of a needle in the catheter and passed through the hood open area and into the underlying tissue. This type of system could be used to create landmarks in the fluorescence image that could be used for a variety of purposes, such as providing landmarks for stitching together multiple standard images to form a mosaic, or for identifying lesion locations at the time of delivery. The targeted dye delivery could also take place outside of the catheter, for example into the pericardium.

Fluorescence imaging could also be used in the case of blood penetrating imaging systems. Wavelength bands in the vicinity of 1.6 microns are known to penetrate blood reasonably well. A dye that with excitation and emission wavelengths in this region could allow improved feature discrimination over a system that relied on reflected light alone. In this case the excitation light could be used to form one image based on the reflection and scattering properties of the tissue, while the fluorescent emission would create a second imaged based on the amount of dye in the tissue. In this case, the ability of a dye to bind to one or more kinds of tissue well, e.g. healthy cardiac wall tissue, while remaining absent in other types, e.g. blood and scar tissue, is critical to the amount of discrimination achieved in the image.

The applications of the disclosed invention discussed above are not limited to certain treatments or regions of the body, but may include any number of other applications as well. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. An imaging catheter, comprising:
   a flexible catheter suitable for intravascular advancement;
   an imager in proximity to a distal end of the catheter, wherein the imager is positioned to visualize a tissue region adjacent to the distal end;
   a sensor in proximity to the distal end wherein the sensor is configured to detect fluorescence from the tissue region;
   an excitation source that is configured to activate the fluorescence from the tissue region and is electrically modulated at a rate that is higher than a video frame rate of the imager; and
   a hood attached to the distal end of the catheter and also defining an open area when the hood is in an expanded configuration, wherein the open area is in fluid communication with a fluid lumen defined through the catheter and with a blood-filled environment through an opening defined by the hood.

2. The catheter of claim 1 further comprising a hood attached to the distal end of the catheter and also defining an open area when the hood is in an expanded configuration, wherein the open area is in fluid communication with a fluid lumen defined through the catheter and with a blood-filled environment through an opening defined by the hood.

3. The catheter of claim 1 wherein the excitation source comprises one or more LEDs.

4. The catheter of claim 1 further comprising a dye containing one or more fluorophores for infusion into the tissue region.

5. A method of identifying perfusion in a tissue region, comprising:
   positioning a distal end of a flexible catheter in proximity to a tisane region of interest, the positioning comprising positioning a hood attached to the distal end of the flexible catheter, the hood having an expanded configuration which defines an open area which is in fluid communication with a fluid lumen through the catheter and with an environment external to the hood through an opening defined by the hood;
   illuminating the tissue region of interest adjacent to the distal end of the catheter via an excitation source such that any fluorophores in the tissue region fluoresce, the excitation source being electrically modulated at a rate that is higher than a video frame rate of an imager used to image the tissue region; and
   detecting a presence of perfusion in the tissue region upon an indication of fluorescence emitted from the tissue region.

6. The method of claim 5 further comprising introducing a transparent fluid into the open area via the fluid lumen such that an opaque fluid within the open area is displaced through the opening of the hood and into the environment.

7. The method of claim 5 further comprising detecting a fluorescence from the tissue region via a detector.

8. The method of claim 7 further comprising characterizing a physiological parameter of the tissue region from the detected fluorescence.

9. The method of claim 8 wherein characterizing comprises determining a degree of ablation transmurality of the tissue region.

10. The method of claim 8 wherein characterizing comprises distinguishing portions of ablated tissue relative to portions of non-ablated tissue.

11. The method of claim 10 further comprising ablating the non-ablated tissue.

12. The method of claim 6 further comprising visualizing the tissue region of interest via an electronic imager.

13. The method of claim 12 wherein the electronic imager comprises a CCD or CMOS imager.

14. The method of claim 5 further comprising introducing a dye into the tissue region of interest prior to illuminating the tissue region, where the dye is selected from the group consisting of endoscein, fluorescein, fluorescein derivatives, Methylene blue, and indocyanine green.

15. A method of enhancing a visual image of a tissue region, comprising:
   positioning a hood attached to a flexible catheter in proximity to a tissue region of
   interest, the hood having an expanded configuration which defines an open area which is in fluid communication with a fluid lumen through the catheter and with an environment external to the hood through an opening defined by the hood;
   introducing a transparent fluid into the open area via the fluid lumen such that an opaque fluid within the open area is displaced through the opening of the hood and into the environment;
   illuminating the tissue region of interest over a visual spectrum;
   visualizing the tissue region of interest through the transparent fluid via an imager positioned within or adjacent to the open area; and,
   enhancing an illumination of the tissue region at a first wavelength of the spectrum and at a second wavelength of the spectrum in contrast to the first wavelength such that a difference in an image of the tissue region is increased.

16. The method of claim 15 wherein enhancing an illumination comprises enhancing the illumination at the first wavelength in a deep blue region of the spectrum.

17. The method of claim 16 wherein enhancing an illumination comprises enhancing the illumination at the second wavelength in a deep red region of the spectrum.

18. The method of claim 17 further comprising enhancing the illumination in a green region of the spectrum to preserve a white balance of the image.

19. The method of claim 15 wherein illuminating the tissue region comprises illuminating via one or more LEDs.

20. The method of claim 19 further comprising electrically modulating the one or more LEDs at a rate above a frame rate of the imager.

21. The method of claim 15 further comprising applying a pattern of one or more filters with transmission peaks corresponding to one or more of the wavelengths over one or more pixels of the imager such that a difference in the image of the tissue region is further increased.

22. The method of claim 15 wherein visualizing comprises increasing a frame rate of the imager to a rate greater than about 30 Hz.

23. The method of claim 15 further comprising introducing a dye into the tissue region of interest prior to illuminating the tissue region, where the dye is selected from the group consisting of endoscein, fluorescein, fluorescein derivatives, Methylene blue, 20 and indocyanine green.

24. A method of enhancing a visual image of a tissue region, comprising:
    positioning a hood attached to a flexible catheter in proximity to a tissue region of interest, the hood having an expanded configuration which defines an open area which is in fluid communication with a fluid lumen through the catheter and with an environment external to the hood through an opening defined by the hood;
    introducing a transparent fluid into the open area via the fluid lumen such that an opaque fluid within the open area is displaced through the opening of the hood and into the environment;
    illuminating the tissue region of interest over a visual spectrum;
    visualizing the tissue region of interest through the transparent fluid via an imager positioned within or adjacent to the open area; and,
    applying one or more filters to the imager such that a responsivity of the imager is enhanced at one or more wavelengths such that a difference in an image of the tissue region is increased.

25. The method of claim 24 wherein applying one or more filters comprises enhancing the responsivity at a first wavelength in a deep blue region of the spectrum.

26. The method of claim 25 wherein applying one or more filters comprises enhancing the responsivity at a second wavelength in a deep red region of the spectrum.

27. The method of claim 26 further comprising enhancing the responsivity in a green region of the spectrum to preserve a white balance of the image.

28. The method of claim 24 wherein the one or more filters are applied in a pattern over one or more pixels of the imager.

29. The method of claim 24 further comprising introducing a dye into the tissue region of interest prior to illuminating the tissue region, where the dye is selected from the group consisting of endoscein, fluorescein, fluorescein derivatives, Methylene blue, and indocyanine green.

* * * * *